US009739778B2

(12) United States Patent
Bruderer

(10) Patent No.: US 9,739,778 B2
(45) Date of Patent: Aug. 22, 2017

(54) DIAGNOSTIC TEST FOR CSFV ANTIBODIES

(71) Applicant: Intervet Inc., Madison, NJ (US)

(72) Inventor: Urs Peter Bruderer, Kleve (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/104,406

(22) PCT Filed: Dec. 18, 2014

(86) PCT No.: PCT/EP2014/078373
§ 371 (c)(1),
(2) Date: Jun. 15, 2016

(87) PCT Pub. No.: WO2015/091736
PCT Pub. Date: Jun. 25, 2015

(65) Prior Publication Data
US 2016/0313330 A1    Oct. 27, 2016

(30) Foreign Application Priority Data
Dec. 19, 2013  (EP) ..................................... 13198615

(51) Int. Cl.
G01N 33/569    (2006.01)
A61K 39/12    (2006.01)
C12N 7/00    (2006.01)
A61K 39/00    (2006.01)

(52) U.S. Cl.
CPC ....... *G01N 33/56983* (2013.01); *A61K 39/12* (2013.01); *C12N 7/00* (2013.01); *A61K 2039/552* (2013.01); *C12N 2710/14143* (2013.01); *C12N 2770/24322* (2013.01); *C12N 2770/24334* (2013.01); *C12N 2800/22* (2013.01); *G01N 2333/183* (2013.01); *G01N 2469/20* (2013.01); *G01N 2800/52* (2013.01)

(58) Field of Classification Search
None
See application file for complete search history.

(56) References Cited

U.S. PATENT DOCUMENTS

2006/0292557 A1   12/2006   Su et al.
2016/0313330 A1*  10/2016   Bruderer .......... G01N 33/56983

FOREIGN PATENT DOCUMENTS

| CN | 102317449 A | 1/2012 |
| EP | 2202298 A1 | 6/2010 |
| WO | WO2010074575 A2 | 7/2010 |

OTHER PUBLICATIONS

Greenspan et al (Nature Biotechnology.1999; 7: 936-937).*

Blome, S. et al., Assessment of classical swine fever diagnostics and vaccine performance, Rev. sci. tech. Off. int. Epiz., 2006, 1025-1038, 25 (3).
Chang, Chia-Yi et al., Antigenic domains analysis of classical swine fever virus E2 glycoprotein by mutagenesis and conformation-dependent monoclonal antibodies, Virus Research, 2010, pp. 183-189, vol. 149.
Cox et al., Immunoassay Methods, Assay Guidance Manual eBook, May 2012, 1-35.
Eblé et al., Efficacy of chimeric pestivirus vaccine candidates against classical swine fever: Protection and DIVA characteristics, Veterinary Microbiology, 2013, 437-446, 162.
Euopean Search report for 13198615.0 dated Feb. 25, 2014, 7 pages.
Ganges, L. et al., A DNA vaccine expressing the E2 protein of classical swine fever virus elicits T cell responses that can prime for rapid antibody production and confer total protection upon viral challenge, Vaccine, 2005, pp. 3741-3752, 23.
Holinka, L.G. et al., Development of a live attenuated antigenic marker classical swine fever vaccine, Virology, 2009, 106-113, 384.
International Search report for PCT/EP2014/078373 dated Mar. 25, 2015, 12 pages.
Kortekaas, J. et al, Protective efficacy of a Classical swine fever virus C-strain deletion mutant and ability to differentiate infected from vaccinated animals, Veterinary Microbiology, 2011, 11-18, 147.
Kortekaas, J. et al, Rational design of a classical wine fever C-strain vaccine virus that enables the differentiation between infected and vaccinated animals, Journal of virological methods, 2010, 175-185, 163.
KPL Inc.; Technical Guide for ELISA; KPL Inc., Gaithersburg, MD 20878; 2013, vol. ML300-05; pp. 1-44. www.kpl.com/ELISA.
Lin, M et al., Deletions of Structural Glycoprotein E2 of Classical Swine Fever Virus Strain Alfort/187 resolve a linear epitope of monoclonal antibody WH303 and the minimal N-terminal domain essential for binding immunoglobulin G antibodies of a pig hyperimmune serum, Journal of Virology, 2000, p. 11619-11625, vol. 74, No. 24.
Moennig V., Introduction to classical swine fever: virus, disease and control policy, Veterinary Microbiology, 2000, pp. 93-102, 73.
Reimann, I. et al., Characterization of a new chimeric marker vaccine candidate with a mutated antigenic E2-epitope, Veterinary Microbiology, 2010, 45-50, 142.
Schroeder S. et al., Evaluation of classical swine fever virus antibody detection assays with an emphasis on the differentiation of infected from vaccinated animals, Rev. sci. tech. Off. int. Epiz., 2012, 997-1010, 31 (3).

(Continued)

*Primary Examiner* — Shanon A Foley

(57) ABSTRACT

The present invention relates to the field of veterinary diagnostics, specifically to a test for the detection of antibodies against CSFV. In particular the invention relates to a method for detecting antibodies against wild type CSFV in a test sample, characterized in that the method comprises co-incubating with a carrier comprising a mutated TAVSPT-TLR epitope of CSFV E2 protein. Further, the invention relates to a diagnostic test kit, and to the use of the method according to the invention. In addition the invention relates to a method for differentiating between animals infected with wild type CSFV and animals that were vaccinated against CSFV with a CSFV (marker) vaccine, and to a method for controlling an infection with wild type CSFV in a population of porcine animals, by the combined use of a CSFV (marker) vaccine and the diagnostic test kit of the invention.

14 Claims, 5 Drawing Sheets

(56) References Cited

OTHER PUBLICATIONS

Figure 1:
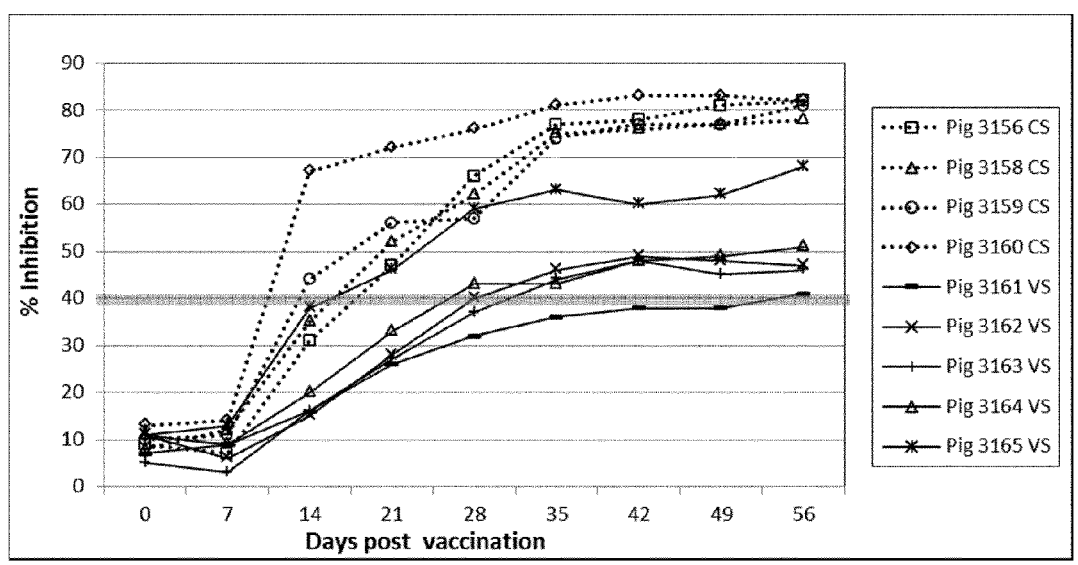
Figure 1:
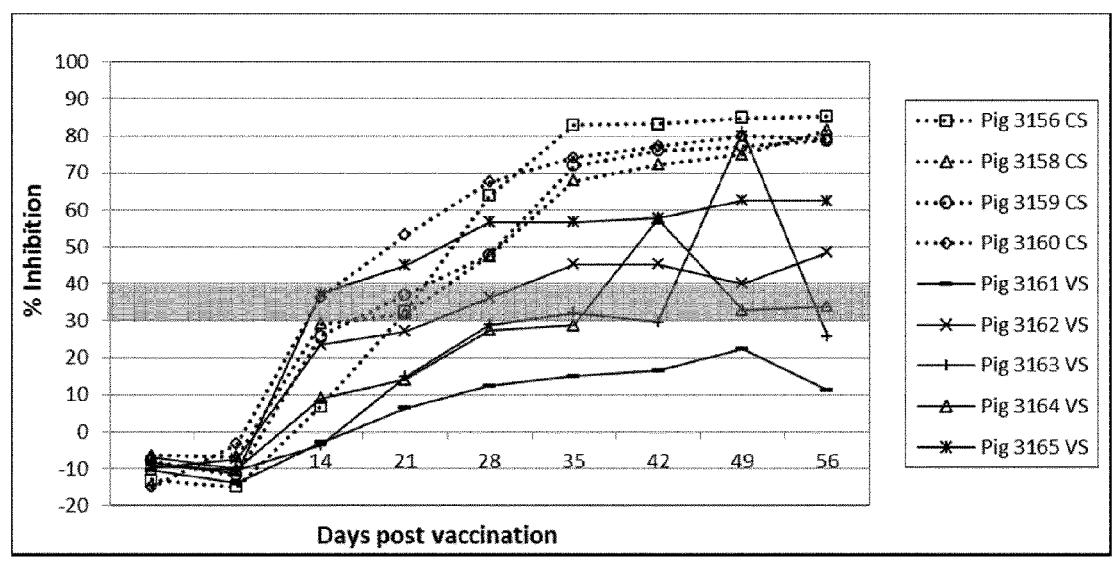
Figure 1:
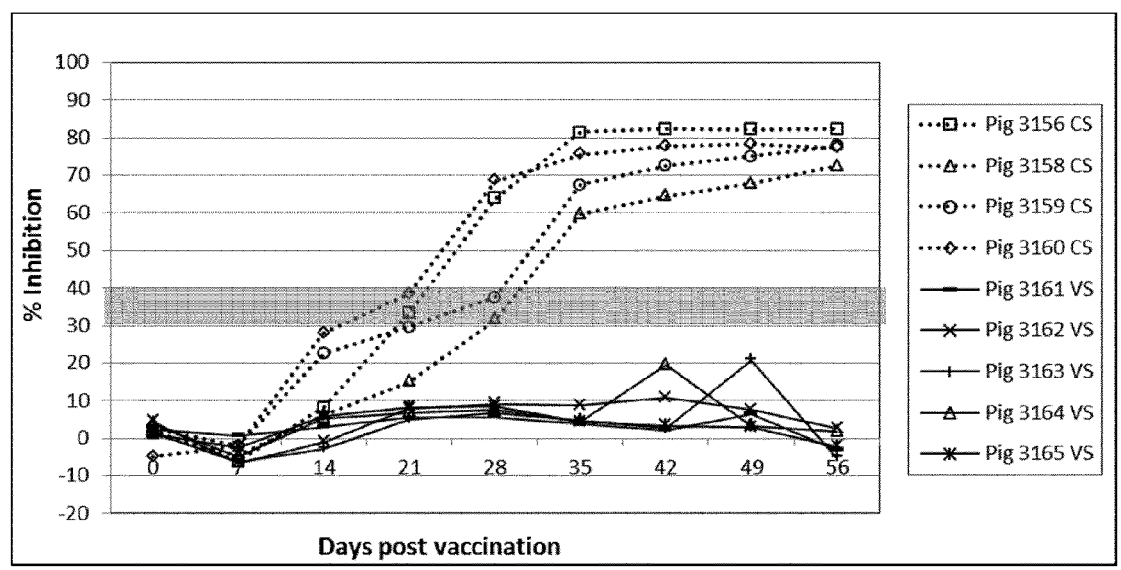

Van Rijn, P.A. et al., Antigenic structure of envelope glycoprotein E1 of hog cholera virus, Journal of Virology, 1994, pp. 3934-3942, vol. 68, No. 6.

Van Rijn, P.A., et al., Epitope mapping of envelope glycoprotein E1 of hog cholera virus strain Brescia, Journal of General Virology, 1993, pp. 2053-2060, 74.

* cited by examiner

DIAGNOSTIC TEST FOR CSFV ANTIBODIES

CROSS-REFERENCE TO RELATED APPLICATIONS

This application is a national stage entry under 35 U.S.C. §371 of PCT/EP2014/078373 filed on Dec. 18, 2014, which claims priority to EP Application No. EP13198615.0 filed on Dec. 19, 2013. The content of PCT/EP2014/078373 is hereby incorporated by reference in its entirety.

The present invention relates to the field of veterinary diagnostics, specifically to a test for the detection of antibodies against CSFV. In particular the invention relates to a method for detecting antibodies against wildtype CSFV in a test sample. Further, the invention relates to a diagnostic test kit, and to the use of the method for detecting antibodies against wildtype CSFV. In addition the invention relates to a method for differentiating between animals infected with wildtype CSFV and animals that were vaccinated against CSFV with a CSFV vaccine, and to a method for controlling an infection with wildtype CSFV in a population of porcine animals.

Different tests are known for the serodiagnosis of infection with a micro-organism, in order to determine if a human or animal is positive or negative for either the micro-organism or for antibodies against the micro-organism. Typically such tests comprise techniques for the detection of immune complexes that may have formed, using a defined antibody to provide specificity. Often the test will also have a step for amplifying the signal strength, and one or more steps for washing away unbound, unspecific or unwanted components. The detection of immune complexes can be in a variety of ways such as optically by detecting a colour change, a fluorescence, or a change in particle size, or alternatively by the detection of radioactively labelled antigens or antibodies in immune-complexes. Similarly, the physical form of the test can vary widely and can e.g. employ a microtitration plate, a membrane, a dipstick, a biosensor chip, a gel matrix, or a solution comprising (micro-) carrier particles such as latex, metal, or polystyreen, etc.

The choice for a particular set-up of such a test is usually determined by the type of input sample, the desired test sensitivity (correctly identifying a positive sample), and -specificity (correctly discriminating between true positive and true negative samples); such properties are dependent of the strength and timing of an immune response, or the presence of a micro-organism. Further the requirements for test economy such as its applicability on a large scale and its costs may be decisive for selection of a particular format.

Well known diagnostic tests are: radioimmuno assays, immunodiffusion, immunofluorescence, immuno-precipitation, agglutination, haemolysis, neutralisation, and "enzyme-linked immuno-sorbent assay" or ELISA. Especially for large scale testing, automation of the liquid handling, the result reading and processing, or both, may be a requirement. This may also require replacing a traditional assay format by a more modern and miniaturised format such as in AlphaLISA™ (Perkin Elmer).

Much used diagnostic tests are enzyme immunoassays, such as ELISA's. These are easily scalable, and can be very sensitive. A further advantage is the dynamic range of its results because samples can be tested in a dilution range. Results are expressed in arbitrary units of absorbance, typically between 0.1 and 2.5 optical density (OD) units, depending on the properties and settings of the technical equipment used for the readout. Routinely appropriate positive and negative control samples are included, and mosttimes samples are tested in multifold. Standardisation is obtained by including (a dilution range of) a defined reference sample, which also allows matching a certain score to preset values for determining positives or negatives, and allows correlation to a biological meaning, for example: an amount of antigen to potency, or an amount of antibody to a level of immune protection.

Many variants of an ELISA set-up are known, but typically employ the immobilisation of an antigen or an antibody to a solid phase, e.g. to a well of a microtitration plate. When an antibody is immobilized the test is called a 'capture' or 'sandwich' ELISA. Next a test sample is added, allowing the ligand (e.g. an antigen or antibody to be detected) to bind. Then a detector (an antibody, antigen, or other binding component) is added which is conjugated to a label, for instance to an enzyme that can induce a colour reaction, which can be read spectrophotometrically. Other types of label could be using luminescence, fluorescence, or radioactivity. The use of a labelled detector is intended to provide amplification of signal strength to enhance test sensitivity, however, it may also introduce background signal, reducing the signal to noise ratio.

In a variant of the ELISA protocol, the test specificity is improved by the introduction of a competitive binding, in which case the test is called a 'competition-', 'interference-', or 'blocking ELISA'. In such an assay a factor in the test sample (an antibody or an antigen) competes with a labelled detector antibody/antigen for binding to a molecule (antigen or antibody) immobilised to the solid phase. This causes a reduction in the maximal colour signal, which is a sensitive way to measure presence or amount of the competing factor. The result can be expressed as a percentage of inhibition of the maximal ELISA signal.

Because of their versatility and sensitivity, ELISA's are used generally, for example for epidemiology, infection surveillance programs, or to verify the efficacy of a vaccination campaign. This use of ELISA also extends to the animal health sector, for example to monitor eradication and control measures of the more relevant infectious diseases. Critical in that context is a sufficient level of sensitivity and specificity of the diagnostic test, as faults in this respect can have grave consequences either way: false positives can cause unnecessary quarantine or culling of animals, and false negatives may cause spread of a pathogen by transport of undetected carrier-animals across borders. One example of such use of ELISA is in the control of an OIE notifiable disease, such as Classical swine fever (CSF) in porcine animals.

CSF, also known as hog cholera or swine fever, is an often fatal disease of porcine animals, which occurs worldwide. It is caused by classical swine fever virus (CSFV), also known as Hog cholera virus, which is highly infectious. The disease causes much animal suffering, and considerable economic losses to sectors dependent on commercial pig farming and their products.

CSFV belongs to the family of Flaviviridea, and to the genus Pestivirus. Well-known other Pestiviruses are Border Disease virus (BDV), infecting sheep and swine, and Bovine Viral Diarrhoea virus (BVDV), infecting cattle, sheep and swine. Some level of cross-protection occurs between these related viruses. The CSF virion is relatively small and enveloped, and comprises the positive sense, single stranded RNA viral genome, of about 12.3 kb. This genome is translated into one large polyprotein of about 4000 amino acids, which is auto-cleaved by a number of non-structural viral proteins. This results in the main structural viral envelope glycoproteins: Erns, E1 and E2. For a review on the virus and its disease, see: Moennig (2000, Vet. Microbiol., vol. 73, p. 93).

The gold-standard for detection of antibodies against CSFV is the virus neutralisation test. However as that is laborious and difficult, ELISA type tests are used for rapid screening and detection, and a variety of commercial tests is available for the detection of CSFV antigen or CSFV antibodies. Such tests are reviewed in Biome et al. (2006, Rev. Sci. Tech. (Int. Off. Epiz.), vol. 25, p. 1025). The tests for CSFV antigen detect either whole virus or specific viral (envelope) proteins, such as Erns or E2. Similarly, tests for CSFV antibodies detect virus-, E2- or Ems antibodies. The detection of antibodies in a target animal is more sensitive than detection of an antigen or virus, because the antibodies are present in the animal for longer time, providing a wider time window for detection. In addition, because of the cross-reactivity among Pestiviruses, diagnostic tests for CSFV based on detection of Erns antigen or -antibodies are not reliable in regions with a high prevalence of BVD and/or BVDV. Therefore the current focus for CSFV diagnosis is on the detection of antibodies against CSFV E2 protein. For a review: Schroeder et al. (2012, Rev. Sci. Tech. (Int. Off. Epiz.), vol. 31, p. 997).

The CSFV E2 protein (previously known as glycoprotein E1, or gp51-54) is encoded from amino acid (aa) position 690 of the CSFV polyprotein. The mature CSFV E2 protein is about 370 aa in length, this is without an N-terminal signal sequence of about 22 aa which overlaps the E1 C-terminus, but includes a C-terminal transmembrane region of about 40 aa (Ganges et al., 2005, vaccine vol. 23, p. 3741). On E2, the immunodominant A domain is located between amino acid positions 766 and 866 of the polyprotein (van Rijn et al., 1993. J. of Gen. Virol., vol. 74, p. 2053). Within that domain one linear B-cell epitope has been identified that elicits virus-neutralising antibodies: the TAVSPTTLR epitope (SEQ ID NO: 1). This epitope is located in the CSFV polyprotein at amino acid positions 829-837, corresponding to aa 140-148 of the E2 aa sequence, and is well conserved among CSFV strains, but does not cross-react with BVDV- or BVD antibodies (Lin et al., 2000, J. of Virol., vol. 74, p. 11619).

A number of commercial E2 antibody tests have been developed that employ the specificity of this epitope: the PrioCHECK® CSFV Ab 2.0 (formerly named the Ceditest® CSFV 2.0) (both: Prionics AG, Schlieren-Zurich, Switzerland), and the IDEXX CSFV Ab Test® (IDEXX Europe B.V., Hoofddorp, The Netherlands). These tests are competition ELISAs that use immobilised CSFV E2 protein. When any E2 antibodies are present in the test sample, they bind to the immobilised CSFV E2, and so compete with a labelled indicator antibody, which is an enzyme-conjugated monoclonal antibody specific for the TAVSPTTLR epitope of wildtype CSFV E2; the labelled monoclonal antibodies used as indicator in these kits are called V2 (Prionics) or A18 (IDEXX), and have the same specificity as the WH303 monoclonal antibody used by Lin et al. (2000, supra).

Vaccines against CSF are known and are being used routinely in countries where CSFV is endemic. As inactivated CSFV vaccines were impractical, since many years live-attenuated virus vaccines have been used; the most effective ones are based on the so-called China- or C-strain. It has a very reliable track record from many years of use, and is also the only live attenuated vaccine allowed in the European Union, although only for emergency vaccinations in case of CSF outbreaks. Often a governmental control program for CSF (e.g. EU Council Directive 2001/89/EC) is backed up by a system of trade restrictions banning the transport of pigs that are seropositive for antibodies against CSFV.

However, some countries may suffer frequent reinfections from the natural reservoir of CSFV in feral pigs and wild boar. Consequently, occasional outbreaks of CSF occur, and many pigs-both infected and non-infected-are culled. This causes much ethical concerns as well as considerable costs. Also, pigs subjected to emergency vaccination may no longer be exported, as they have become seropositive. This causes overcrowding of stables and further economic losses.

Therefore, efforts focussed on the development of vaccines that allow the serologic "differentiation of infected from vaccinated animals" or: DIVA. The basic principle behind this type of discriminating test is that the vaccination of a target animal with a vaccine that has a positive or negative 'marker' function can be differentiated serologically from the infection of an animal with the wildtype micro-organism. For example the marker vaccine may be deficient in one or more antigens that are present in the wildtype micro-organism. An infected target will then become seropositive for that antigen while vaccinates remain seronegative for that antigen.

One class of DIVA vaccines developed for use against CSF are based on viral subunits such as E2 and/or Ems. However these are less protective, and have a slower onset of immunity than whole virus vaccines.

Also, under a regime of non-vaccination and stamping-out of CSFV, the only way such a CSFV marker vaccine would be allowed on the market, is in a combination with a reliable companion diagnostic test.

In an effort to combine into one vaccine a strong and early protection, as well as DIVA capability, the existing C-strain live attenuated CSFV vaccine was modified with recombinant DNA techniques by Kortekaas et al. (2010, J. of Virol. Methods, vol. 163, p. 175), whereby they focussed on the TAVSPTTLR epitope in the A domain of the CSFV E2 protein. Some amino acids in the epitope were mutated or deleted, after which the mutant CSFV virus was submitted to forced virus evolution. Viable mutant viruses were obtained having different mutations of the TAVSPTTLR epitope.

Of the vFlc-ΔPT series of C-strain CSFV mutants of E2, one was selected for further study, named: vFlc-ΔPTa1. This virus has a mutated version of the TAVSPTTLR epitope of E2, by substitution of one, and deletion of two amino acids, the epitope corresponding to the original TAVSPTTLR epitope then became: TAGSTLRTE (SEQ ID NO: 2). This mutant virus showed good viability, and induced a strong antibody response against E2. In addition, rabbit antibodies against the mutated E2 did no longer recognise the wildtype E2 of the parental C-strain virus. Consequently this was considered the ideal candidate for an effective live CSFV marker vaccine that allows DIVA.

The vFlc-ΔPTa1 mutant virus was then tested for vaccine efficacy in the target animal (Kortekaas et al., 2011, Vet. Microbiol., vol. 147, p. 11), where it was found to induce a level of protection close to that of the parent strain, and effectively prevented shedding of challenge virus. However, the authors were disappointed to find that the sera from pigs vaccinated with this mutant virus could not clearly be differentiated from sera from pigs vaccinated with parental C-strain virus. This is because the E2 mutant virus induced in pigs antibodies that gave intermediate- to full strength false positive scores in the E2 ELISA. Consequently this ruled out the market introduction of a new DIVA marker vaccine, for lack of a reliable discriminatory CSFV antibody test.

In trying to overcome the false positive scores in the E2 ELISA on sera from pigs vaccinated with a marker vaccine, Kortekaas et al. (2011, supra) considered several amendments to the ELISA, such as: modification of the peptides used by using tertiary structure predictions; use of new monoclonal antibodies that would allow better differentiation; change of the ELISA using different blocking antibodies, as this had proven effective for others (Holinka et al., 2009, Virology, vol. 384, p. 106); and: change of the cut-off value for the read-out, while keeping acceptable sensitivity. All these approaches were found to be ineffective to overcome the occurrence of false positives.

Figure 3:
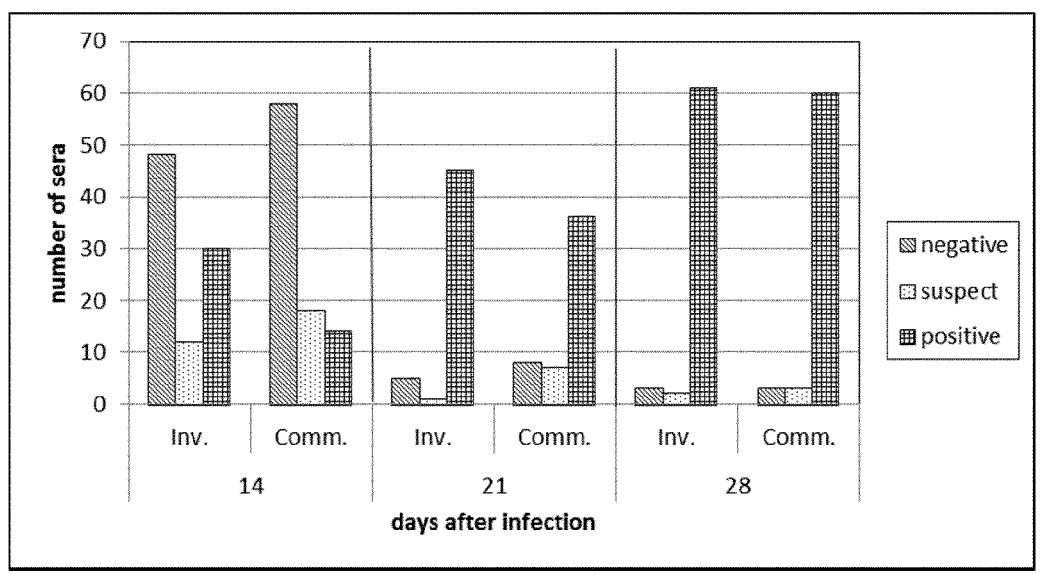

As indicated, the results of Holinka et al. (2009, supra) did not show false positive results in a similar E2 ELISA, when testing sera from pigs vaccinated with a different recombinant CSF marker. However their results cannot be considered to be significant: on the one hand because they tested pooled rather than individual sera, and on the other because their readings are in the bottom range of detection (between 0.100 and 0.350 OD units; see Holinka et al., 2009, supra; FIG. 3A), where the signal-to-noise ratio is too unfavourable to form the basis for a reliable large scale diagnostic test.

A better example is the publication by Reimann et al. (2010, Vet. Microbiol., vol. 142, p. 45), who constructed a recombinant CSF vaccine much alike that of Holinka et al., by replacing the TAVSPTTLR epitope from CSFV E2 by the corresponding sequence from BVDV E2. In line with the results of Kortekaas et al. (2011, supra), Reimann et al. also found cross-reactive antibodies in the sera of pigs vaccinated with their mutated E2 virus, that bound to unmodified E2 epitope. So also in this case, false positive scores were obtained, and a DIVA test could not be developed. To address this problem Reimann et al. suggested adapting cut-off values at a cost to sensitivity, or modifying the mutant virus backbone sequence to reduce false positive scores.

So, different mutations to the TAVSPTTLR epitope were found to cause the same issues for a CSFV marker vaccine based on such a mutant epitope: in the case of a CSFV vaccine based on the vFlc-ΔPTa1 virus, the mutations to the TAVSPTTLR epitope changed 6 of the 9 amino acids in that locus. Similarly, for Reimann et al. (2010, supra), testing 5 different amino acids of the 9 in the corresponding locus of the E2 protein, this problem also occurred.

Consequently, the problem of the false positive scores in an ELISA for wildtype CSFV E2 antibodies in sera obtained from animals vaccinated with a CSFV (marker) vaccine comprising a mutated TAVSPTTLR epitope of the CSFV E2 protein, is therefore of a general nature, and until today, has still not been overcome. In a recent review of CSF vaccine candidates, Eblé et al. (2013, Vet. Microbiol., vol. 162, p. 437) confirm this dilemma that for CSFV the optimal combination of a CSFV vaccine and corresponding DIVA test is not yet available.

It is therefore an object of the present invention to overcome disadvantages in the prior art, and to accommodate to a need in the field by reducing false positive results in diagnostic assays for antibodies against wild type CSFV, when testing samples from animals that were vaccinated with a CSFV vaccine having a mutation in the TAVSPTTLR epitope of CSFV E2.

Surprisingly it was found that this object can be met, and consequently disadvantages of the prior art can be overcome, by an improved diagnostic test for wildtype CSFV antibodies, which allows DIVA. The improvement regards the modification of an incubation step of a diagnostic assay for wildtype CSFV E2 antibodies, wherein a test sample is incubated with an immobilised carrier comprising a TAVSPTTLR epitope of CSFV E2, and now incorporates the co-incubation with a carrier comprising a mutated TAVSPTTLR epitope of CSFV E2. This modification was found to totally reduce false positive results, by only a limited modification to the protocol of an existing diagnostic assay for CSFV E2 antibodies.

The advantageous effects of this modified diagnostic method are several: the main one being that this modification can be completely integrated into the existing test protocol. Consequently, no additional incubation step is required, and the improved test method does not require more time than previously. This is a significant advantage, considering the potentially very large numbers of test samples that may need to be tested in a short time in the instance of a CSF outbreak in an area.

Further it is now no longer necessary to make drastic changes to the corresponding CSFV vaccine or to the original diagnostic assay. On the contrary, it is now possible to use the basic set-up of an existing CSFV E2 ELISA, for the detection of wildtype CSFV E2 antibodies in samples from animals vaccinated with a CSFV vaccine. This allows the reliance on the established CSFV diagnostic assays with their proven reliability, and well-established specificity- and sensitivity profiles.

With this modification a CSFV diagnostic assay can now be used to effectively distinguish between infected and vaccinated animals, and thus the invention provides an improved diagnostic test for wildtype CSFV, which allows DIVA screening, and can be used as companion diagnostic for a CSFV (marker) vaccine, to control occurrence of CSFV in a susceptible population of animals.

An important step towards these advantageous effects was the identification by the inventor of the cause for the failure to discriminate vaccination against CSFV, from infection with wildtype CSFV, or with C-strain vaccine.

This cause was found to be that a CSFV (marker) vaccine comprising an E2 with a mutated TAVSPTTLR epitope, induces antibodies that can bind specifically not only to the mutated E2 epitope of the vaccine, but also—and with equally high affinity—to the unmodified TAVSPTTLR epitope of E2 in wildtype CSFV, and in the C-strain vaccine. This caused false positive scores when testing serum samples of vaccinated animals for infection with wildtype CSFV. In contrast, antibodies resulting from infection with wildtype CSFV, or inoculation with a C-strain vaccine, or monoclonal antibodies against the wildtype TAVSPTTLR E2 epitope (e.g.: V2 (Prionics), A18 (IDEXX), or WH303 (Lin et al., 2000, supra)), were not found to have any significant affinity for the E2 protein with mutated TAVSPTTLR epitope of a CSFV vaccine. That was why co-incubation with a carrier comprising a TAVSPTTLR epitope of wildtype CSFV E2 protein did not solve the issue of false positive scores against the vaccine with mutated TAVSPTTLR epitope.

It is currently not known how or why this phenomenon occurs. However, without being bound to any theory or model that would explain these observations, the inventor speculates there is an influence of the three-dimensional form of the TAVSPTTLR epitope of CSFV E2; this 3D form is changed upon mutation of its linear amino acid sequence. This induces antibodies against the mutant E2 epitope, which apparently are still able to bind specifically to the wildtype TAVSPTTLR epitope of CSFV E2. Such antibodies are cross-reactive in a diagnostic assay based on wildtype CSFV E2 protein, causing highly specific false positive scores.

With this insight into the cause of the problem of the false positive test scores, the inventor then found a surprising way to address this problem, and was able to implement a solution into one step of the protocol of an established E2 diagnostic assay: the step for incubating a test sample with an immobilised carrier comprising a TAVSPTTLR epitope of the CSFV E2 protein, and in addition: co-incubating with a carrier comprising a mutated TAVSPTTLR epitope of the CSFV E2 protein. This solved the issue of false positive scores.

The fact that the modification of the diagnostic method can take the form of a co-incubation was a surprise, as such a procedure would normally be expected to be disruptive to the proper and complete binding of CSFV E2 antibodies in the test sample with the immobilised carrier comprising a TAVSPTTLR epitope of CSFV E2, and thus would normally not be considered by a skilled person.

Therefore in a first aspect the invention relates to a method for detecting antibodies against wildtype classical swine fever virus (CSFV) in a test sample, whereby said sample may also comprise antibodies against a mutated TAVSPTTLR epitope of CSFV E2, the method comprising a step for incubating said test sample with an immobilised carrier comprising a TAVSPTTLR epitope of CSFV E2, characterised in that the method comprises co-incubating in said step with a carrier comprising a mutated TAVSPTTLR epitope of CSFV E2.

The "method for detecting" according to the invention is an in vitro method, applied on a test sample, to determine a value or property (often called a 'biomarker') of a test sample, after which the result of the assay can be interpreted to give a certain meaning to its outcome. This interpretation is based on comparison of the result obtained for a test sample using the method, to a reference value or previous measurement, and establishes if the value measured is present or absent, or has increased or decreased.

For the invention, the value measured is the qualitative and quantitative presence of antibodies specific for the TAVSPTTLR epitope of wildtype CSFV E2 protein.

The method according to the invention can be a diagnostic test in one of different well known forms, e.g. as: radioimmuno-, immunodiffusion-, immunofluorescence-, immunoprecipitation-, agglutination-, haemolysis-, neutralisation assay, "enzyme-linked immuno-sorbent assay" (ELISA), or AlphaLISA™.

Several textbooks describe the variety of diagnostics tests that is available and their specific features; for example: J. Huebner: Antibody-antigen interactions and measurements of immunologic reactions (Chapter 9 in: Pier, Lyczak and Wetzler (eds): Immunology, infection, and immunity, ASM Press, Washington D.C., 2004, ISBN: 1555812465, p. 207-232); 'Antibodies: A Laboratory Manual' (eds.: Harlow and Lane, Cold Spring Harbor Laboratory Press, 1988, ISBN-10: 0879693142); and: 'Immunoassays: A Practical Approach' (J. P. Gosling edt., Oxford University press, 2000, ISBN-10: 0199637105).

A large number of commercial companies can provide materials and reagents for diagnostic testing, or complete diagnostic kits, or can provide for the testing and analysis.

It is well within the routine capabilities of the skilled person to devise and optimise the protocol, materials, and the conditions for a method according to the invention.

As is also well known in the art, "antibodies" are immunoglobulin proteins, and generally exist in 5 classes. For the test sample, the antibodies will typically be of IgG or IgM type, and be whole antibodies. However the other antibodies that can be used as a reagent in a method according to the invention, for example as a secondary antibody, or as labelled antibody, do not need to be whole immunoglobulins e.g. a single chain antibody, or a part of an immunoglobulin; and can also be of a different form: a (synthetic) construct of such parts, provided the antibody-parts still contain an antigen-binding site. Well known sub-fragments of immunoglobulins are: Fab, Fv, scFv, dAb, or Fd fragments, Vh domains, or multimers of such fragments or domains.

Antibodies for use as reagent in diagnostic assays are commonly produced by (over-)immunising a donor animal with the target antigen, and harvesting the antibodies produced from the animal's serum. Well known donors are rabbits and goats. Another example is chickens which can produce high levels of antibodies in the egg-yolk, so-called IgY. Alternatively, antibodies can be produced in vitro, e.g. via the well-known monoclonal antibody technology from immortalized B-lymphocyte cultures (hybridoma cells), and for which industrial scale production systems are known. Also antibodies or fragments thereof may themselves be expressed in a recombinant expression system, through expression of the cloned Ig heavy- and/or light chain genes. All these are well known to the skilled artisan.

For the invention and throughout this text, antibodies will be referred to based on the target against which they are directed; e.g.: antibodies against CSFV are referred to as 'CSFV antibodies', and 'E2 antibodies', are antibodies against E2 protein a.k.a. anti-E2 antibodies, etc.

As is well known in the art, antibodies directed "against" a certain target, are antibodies that are specific for an epitope on that target, whereby the target is a particular molecule or entity. An antibody (or fragment thereof) is specific for an epitope if it is capable of selective binding to that epitope.

Whether the interaction between an antibody and a target is specific and/or selective or not, can easily be assessed by a skilled person. For example, the specificity of results of an inhibition based immune-assay can be determined by demonstrating the inhibition is correlated with the concentration of the antigen or of the antibody used in the assay. Using e.g. a competition binding assay, it can be determined how much of an antigen is required to inhibit antibody binding to this coated antigen by 50% (Bruderer et al., 1990, J. of Imm. Meth., vol. 133, p. 263). As an example for the present case: using the wildtype CSFV E2 protein, and the TAVSPTLLR epitope-specific (monoclonal) antibody.

Very relevant in the context of a diagnostic immunoassay, is when an antibody demonstrates false positive binding, leading to false positive results of the diagnostic assay. This may be caused by a relatively strong binding to an epitope other than the one the antibody was generated against, or by a specific binding to its originating epitope, but then located on a different target then the originating target.

A person skilled in the field of immunoassay techniques knows how to differentiate true and false positive results, for example by confirmation of the results with a different type of diagnostic assay, or confirmation of the result with a test sample from a different time point.

By the method according to the invention, significant reductions in false positive scores can be obtained when testing for antibodies against E2 protein of wildtype CSFV. As outlined and exemplified herein, reduction of false positive scores have been reached of up to 5 fold (e.g. from more than 50% ELISA inhibition, down to less than 10% inhibition), and of up to 100% reduction of the number of animals incorrectly considered CSFV positive.

In various tests using a method according to the invention, all sera from pigs infected with wildtype CSFV were qualified as positive, based on the test results, from about 3 weeks after infection, whereas none of the sera from animals vaccinated repeatedly with a vaccine based on vFlc-ΔPTa1, became positive after the third vaccination, until the last time point measured.

The method according to the invention was also tested on a large set of about 900 test samples from the collection of the Central Veterinary Institute (Lelystad, the Netherlands), comprising CSFV antibodies that were high, low, negative, or suspect, as well as a number of sera containing BVD- or BVDV-antibodies, and even some mixed infections of CSFV, BVD, and/or BVDV. By the method according to the invention, almost all samples could be identified correctly, with excellent specificity and sensitivity, see the Examples hereafter.

In fact, when testing the 900 sample collection, even an enhanced sensitivity was observed for most of the samples tested when applying co-incubating with the method according to the invention. This means that the percentage of inhibition observed in a blocking ELISA for wildtype CSFV E2 antibodies was higher for several of the samples when the method according to the invention was applied, as compared to applying a standard commercial CSFV E2 antibody blocking ELISA. This resulted in 5 samples previously indicated as suspect now scoring positive, and two previously negative samples now scoring suspect (see Example 2.3, and Table 2).

For the invention "wildtype" classical swine fever virus refers to a CSFV as it would occur in nature. This does not mean such wildtype CSFV are all the same, as many variations in genetic composition and biological features are conceivable or already known. However, this term intends to exclude for use in the invention, those CSFV that are the result of human intervention, such as by modification, or mutation, for example by repeated passaging or by adaptation of its nucleic acid by recombinant DNA techniques.

For the invention "classical swine fever virus" or "CSFV" refers generally to viruses from the taxonomic genus Pestivirus, having the well-known characteristics of CSFV. This includes also CSFV that are sub-classified therefrom in any way, for instance as a subspecies, strain, isolate, genotype, serotype, serovar, serogroup, variant, or subtype and the like. Such CSFV share the characterising features of their taxonomic family-members such as the genomic, physical, electron-microscopic, and biochemical characteristics, as well as biological characteristics such as physiologic, immunologic, or pathogenic behaviour. Next to serological classification, other determinations can be based on nucleotide sequencing or PCR assays, as known in the field.

It will be apparent to a skilled person that while the viral species that is a subject of the present invention is currently named CSFV, this is a taxonomic classification which could be subject to change as new insights lead to reclassification into a new or different taxonomic group. However, as this does not change the micro-organism involved or its characterising features, only its scientific name or classification, such re-classified organisms remain within the scope of the invention.

The "test sample" for use in the method according to the invention, can in principle be any type of sample containing antibodies, for example a plasma- or a serum sample prepared from a sample of whole blood from an animal. The skilled person is well aware of techniques and materials required to obtain and prepare such a plasma or serum sample from an animal.

Preferred is a serum sample, as that is cleaner, and can be prepared by standard laboratory techniques, for example comprising steps for: clotting, centrifugation, and complement inactivation.

Optionally the test sample can be processed or purified further, e.g. to improve signal strength, or to reduce background signal. For example the antibodies can be isolated out. Well known techniques for antibody purification are for example the precipitation of such antibodies using Caprilic acid, or Ammonium Sulphate, or the use of affinity chromatography.

For the invention, the term "comprise" (as well as variations such as "comprising", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprise" (or its variations) is replaced by terms such as "consist of", "consisting of", or "consist essentially of".

A "TAVSPTTLR epitope of CSFV E2" refers to the well-known epitope in the A domain of CSFV E2 protein with that name, and is a linear epitope of 9 amino acids in length. It will be clear to a skilled person that the name "TAVSPTTLR" given to this epitope matches the amino acid sequence of this epitope when that is presented in the standard one letter IUPAC code, in which Threonine is referred as T, Alanine as A, etc.

The TAVSPTTLR epitope of CSFV E2 is conserved in wildtype CSFV (Lin et al., 2000, supra), and its amino acid sequence is represented herein as SEQ ID NO: 1.

For the invention, a "mutated" TAVSPTTLR epitope of CSFV E2, differs in its amino acid sequence in at least one position from SEQ ID NO: 1. The mutation can involve a single or a multiple change, and can be an insertion, a deletion, or a substitution, of an amino acid, or a combination thereof.

An example of a mutated TAVSPTTLR epitope of CSFV E2, for use in the method according to the invention is the corresponding epitope present in the E2 protein of a mutant CSFV virus such as vFlc-ΔPTa1, where this epitope is: TAGSTLRTE (SEQ ID NO: 2). Another example is a recombinant CSFV as described by Reimann et al. (2010, supra), e.g. virus pA/CP7_E1E2alf_TLA, where the corresponding epitope is: TLANKDTLA (SEQ ID NO: 3).

A mutated TAVSPTTLR epitope of CSFV E2, for use in the method according to the invention, can be obtained from a variety of sources, either natural or synthetic. Most convenient is to introduce a mutation in the TAVSPTTLR epitope of a CSFV E2 by human intervention, such as by modification, or mutation, for example by adapting the encoding nucleotide sequence via recombinant DNA technology, followed by expression of a protein (e.g. a CSFV E2 protein, or a part thereof) comprising the mutated epitope in an in vitro recombinant expression system.

For the invention, "incubating" refers to allowing the binding between an antibody and its specific epitope. This will require reaction conditions that are conducive to the formation of such molecular interactions, and will comprise the use of the correct buffers, temperature and duration. Materials and methods for incubating for the invention are described in well-known handbooks, and in the instructions provided by suppliers of commercial tests.

A "carrier", in the context of the present invention refers to a macromolecular structure that can carry and present an epitope of CSFV E2 protein. In principle any structure may be suitable, provided the epitope is accessible for binding with an antibody. The carrier can be biological or mineral in origin, natural or synthetic, large or small, and can for example be a metal particle, a polymer, a protein, or a carbohydrate. The epitope can be attached by covalent bonds, or by non-covalent bonds, including any kind of ionic, electrostatic, hydrodynamic, or molecular interaction. The epitope is comprised in- or on the carrier, and can thus be a part of it, for example as an internal element in a protein, or as a fusion protein. The carrier may also contain other molecules or groups, such as a when a protein comprising the epitope is a lipo- or glycoprotein, or a conjugate, etc. Methods for attaching the epitope to a carrier are well known in the art, and can comprise biochemical- or recombinant DNA techniques.

For the invention, a protein is a molecular chain of amino acids. The protein can be a native or a mature protein, a pre- or pro-protein, or an immunogenic fragment of a protein. Inter alia: peptides, oligopeptides and polypeptides are included within the definition of protein.

The carrier for the invention is "immobilised", meaning: attached to a solid phase, by covalent- or by non-covalent bonding such as by adsorption or coating or the like. This does not imply that the solid phase itself is immobile. The solid phase can in principle be any solid support, provided it allows the performance of the method for detection according to the invention, and may be of different size, shape or form, for example a plate, a particle, a membrane etc.

Methods and materials for immobilising a carrier to a solid phase are well known in the art, and may e.g. involve the use of a Carbonate buffer and a basic pH value. Alternatively the immobilisation can e.g. be via a chemical reaction causing covalent bonding, or via biotinylation of a carrier and binding to an avidin coated solid support.

Preferably the solid phase is a well of a micro-titration plate, or a carrier bead for use in an AlphaLISA assay.

For the invention "co-incubating" indicates that a carrier comprising a mutated TAVSPTTLR epitope of CSFV E2 is incubated together with an immobilised carrier comprising a TAVSPTTLR epitope of CSFV E2 and a test sample. In practice this will mean that a carrier comprising a mutated TAVSPTTLR epitope of CSFV E2 is present in the incubation mixture that is applied in the step for incubating an immobilised carrier comprising a TAVSPTTLR epitope of CSFV E2 and a test sample, for at least a substantial part of the time that is required for that incubation. How much time constitutes 'a substantial part' depends on the details of the particular protocol for the diagnostic assay employed. For example, the manufacturer's instructions of the IDEXX CSFV Ab test, indicate the time period for the step for incubating the test sample and the immobilised E2 protein, is either 2 hours or overnight (12-18 hours).

For the invention 'a substantial part of the time' refers to at least 25% of the time for the step for incubating an immobilised carrier comprising a TAVSPTTLR epitope of CSFV E2 and the test sample. Preferably 50% of the time, more preferably 75, 90, 95, 99, or 100% of the time, in that order of preference.

This co-incubation sets the method according to the invention apart from an incubation that would be considered as a pre-incubation, which would employ a separate and additional step for incubating a test sample and a carrier comprising a mutated TAVSPTTLR epitope, and that would be done prior to the incubation with the immobilised carrier comprising a TAVSPTTLR epitope of CSFV E2. Such a pre-incubation would be the standard choice for a skilled person when optimising incubation protocols, as it allows good control possibilities for reducing any unwanted binding reactions. It is however the surprising finding of the present invention that these incubations can advantageously be integrated into one step as a co-incubation, without detrimental effect to the test's selectivity and specificity.

As described, one of the prominent advantages is that co-incubating does not require additional time for the diagnostic assay to be performed. A further advantage is that the basic protocol of a standard commercial E2 ELISA can be used without significant amendments to the test components or its protocol.

In an embodiment of the method according to the invention, the detection is by enzyme immuno-assay, more preferably by ELISA (enzyme linked immunosorbent assay).

ELISA's are well known, and a variety of types in format and protocol are known. General advantages are that they provide rapid and reliable results, and can easily be scaled up.

In a preferred embodiment of the method according to the invention, the ELISA is an indirect blocking ELISA. As is known in the art, this implies that an antibody from a test sample is competing with a labelled detector antibody for binding to an immobilised epitope. The more antibodies are present in the test sample, the more of it binds to the immobilised epitope, and the less labelled antibody can be retained, resulting in a reduction (inhibition) of the maximal level of label binding.

An exemplary protocol for a method according to the invention whereby the detection is by indirect blocking ELISA, can comprise some or all of the consecutive steps for:

coating of a carrier comprising a TAVSPTTLR epitope of CSFV E2 to a solid phase, co-incubating a test sample and a carrier comprising a mutated TAVSPTTLR epitope of CSFV E2, with the coated carrier, followed by wash, incubating with a labelled secondary antibody, followed by wash, colouring reaction, and reading of the results.

Some of the steps can be performed separately, or by a different party. For example, when applied as a commercial test, a commercial supplier may provide pre-coated solid phase, ready for use in co-incubating with a test sample.

Optionally the protocol may additionally contain one or more steps for blocking-off false positive binding reactions. Typically this involves incubation with an excess of an aspecific protein in a buffer used for incubation- and/or washing steps, e.g. skimmed milk, or serum albumin.

An ELISA can be further optimised by the adaptation of its reagents and process steps, such as the temperature and duration of the incubation steps; the specificity and type of the antibody or antigen used for immobilisation or for detection; the amount and the method of immobilisation applied; and the composition of the incubation- and wash buffers used.

General references to enzyme immunoassays exist in a variety of publications, among others in standard laboratory text books, such as: The Immunoassay Handbook (4th ed.: Theory and applications of ligand binding, ELISA and related techniques'; D. G. Wild edt., 2013, ISBN-10:

0080970370); and: The ELISA Guidebook' (Methods in Molecular Biology, vol. 149, J. R. Crowther, Humana Press, 2000, ISBN-10: 0896037282). Alternatives are manuals from commercial suppliers such as: "Technical guide for ELISA", KPL Inc., Gaithersburg, Md., USA, 2013; and: "Assay guidance manual" by Eli Lilly & Co., chapter: Immunoassay methods, K. Cox et al., May 2012.

In a further preferred embodiment, the ELISA of the invention is essentially similar to a commercial ELISA for CSFV E2 antibodies, for example: to the PrioCHECK® CSFV Ab 2.0 ELISA, formerly named the Ceditest® CSFV 2.0 ELISA, both available from Prionics AG (Schlieren-Zurich, Switzerland), or to the IDEXX CSFV Ab Test, available from IDEXX Europe B. V. (Hoofddorp, The Netherlands). 'Essentially similar' in this respect refers to the protocol and the materials used for these commercial tests.

Alternate protocols for a method according to the invention can also be devised. For example the method according to the invention can be set-up based on the characteristics of the protocol of an AlphaLISA test, well known in the art. In such a test, no wash steps are required and while the assay can be performed manually, an automated AlphaLISA is preferred.

The characteristics of an AlphaLISA protocol are that an antigen (here: a carrier comprising the TAVSPTTLR epitope of CSFV E2) and an antibody (here: a (monoclonal) antibody specific for the TAVSPTTLR epitope of CSFV E2) are bound to carrier beads, and their binding is detectable by light emission.

The carrier comprising the TAVSPTTLR epitope of CSFV E2 can for example be biotinylated and immobilised on an avidin-coated acceptor bead, and used together with an antibody that is conjugated to donor beads. One step in such an AlphaLISA test would then comprise co-incubating acceptor beads coated with the carrier comprising the TAVSPTTLR epitope of CSFV E2 with a test sample and a carrier comprising a mutated TAVSPTTLR epitope of CSFV E2. The other way around (the carrier comprising the comprising the mutated TAVSPTTLR epitope of CSFV E2 is coated), or an intermediary form, whereby both carriers are coated, are equally feasible. The next step could then be an incubation with antibody-coated donor beads, and finally the read out of the results.

Therefore, in an embodiment of the method according to the invention, the detection is by a diagnostic test having the characteristics of an AlphaLISA®.

The method according to the invention is most advantageous for testing samples derived from animals that are susceptible to infection with CSFV. These are various animals of the porcine family.

Therefore, in an embodiment of the method according to the invention, the test sample is derived from a porcine animal.

For the invention "porcine" refers to animals of the family of Suidae, and preferably to animals of the genus Sus, for example: a wild or a domestic pig, swine, hog, wild boar, babirusa, or warthog. This also includes porcines indicated by an arbitrary name referring to their sex or age such as: sow, boar, hog, gilt, weaner, or piglet.

A further advantageous application of the method according to the invention is in testing samples of porcine animals that had been vaccinated against CSFV with a CSFV marker vaccine.

As is well known and described above, the antigen in a marker vaccine differs antigenically from the wildtype antigen it is based on, for example in lacking an epitope, or having a different version of an epitope as compared to the wildtype version. Typically an antigen in a marker vaccine has been adapted or modified by biochemical- or recombinant DNA techniques, and the result is that an antibody response against the modified antigen of the marker vaccine can be differentiated from an antibody response to the unmodified wildtype antigen. This will allow the serologic "differentiation of infected from vaccinated animals" or: DIVA.

Therefore, in an embodiment of the method according to the invention, the test sample is derived from a porcine animal that had been vaccinated against CSFV with a CSFV marker vaccine.

A particularly favourable application of the method according to the invention becomes apparent when the CSFV (marker) vaccine comprises as CSFV antigen a CSFV E2 protein that deviates from the wildtype E2 by a mutation in the TAVSPTLLR epitope of CSFV E2. As described above, in samples of animals vaccinated with such a vaccine, false positives scores were found when using existing diagnostic tests for CSFV antibodies. However the method according to the invention displayed only true positive scores. This has major implications for the veterinary health and the economics of pig-farming.

Therefore, in a preferred embodiment of the method according to the invention, the test sample is obtained from a porcine animal that had been vaccinated against CSF with a CSFV vaccine comprising a CSFV E2 protein comprising a mutated TAVSPTTLR epitope.

As described above, in principle many forms of a mutated TAVSPTTLR epitope of CSFV E2 are conceivable for use in co-incubating for the method according to the invention. However, this method is most advantageously applied in case the mutated TAVSPTTLR epitope of CSFV E2 that is employed in the co-incubation, is the same as that in a marker CSFV vaccine.

Therefore, in an embodiment of the method according to the invention, the mutated TAVSPTTLR epitope of CSFV E2 that is comprised in the carrier for use in co-incubating for the method according to the invention, is the same as the mutated TAVSPTTLR epitope that is present in the CSFV E2 protein of a CSFV marker vaccine.

A further consideration applies to the mutated TAVSPTTLR epitope of CSFV E2 in the CSFV marker vaccine: this vaccine must still be able to induce an effective immune response against CSFV in a target animal, in spite of the mutation to the TAVSPTTLR epitope.

For the invention, there preferably is a match between on the one hand the mutated TAVSPTTLR epitope of CSFV E2 in the CSFV marker vaccine that is used to vaccinate the animals from which a test sample is derived that is to be tested in the method according to the invention, and on the other hand the mutated TAVSPTTLR epitope of CSFV E2 that is comprised in the carrier for use in co-incubating for the method according to the invention.

Therefore, in an embodiment of the method according to the invention, the mutated TAVSPTTLR epitope of CSFV E2 that is comprised in the carrier for use in co-incubating, is the same as the mutated TAVSPTTLR epitope comprised in the CSFV E2 protein of a CSFV vaccine that was used to vaccinate the porcine animals from which the test sample was obtained.

A skilled person is perfectly able to determine which mutated TAVSPTTLR epitopes allow a CSFV marker vaccine comprising a CSFV E2 protein comprising such mutated epitope, to be an effective immunogen. For instance by monitoring the immunological response following vaccination, or after a challenge infection, e.g. by monitoring the targets' clinical signs of disease, clinical scoring, serological parameters, or by re-isolation of the pathogen, and comparing these results to responses seen in mock vaccinated animals.

NB: As CSFV is highly infectious, and is a notifiable disease in many countries, any laboratory- or zootechnical use of samples possibly containing infectious CSFV (either wildtype or attenuated) must be performed with appropriate biosafety precautions, in line with national- or international guidelines.

Examples of CSFV vaccines that comprise a CSFV E2 protein with a mutated TAVSPTTLR epitope of CSFV E2 that can be matched to the carrier comprising the mutated TAVSPTTLR epitope of CSFV E2 for use in co-incubating for the method according to the invention, are known in the art and are described above. For example from Kortekaas et al. (2010, supra); one example being the mutant CSFV named vFlc-ΔPTa1, which has a CSFV E2 protein comprising a mutated TAVSPTTLR epitope with the amino acid sequence: TAGSTLRTE, as presented in SEQ ID NO: 2.

Another example is from Reimann et al. (2010, supra): the mutant CSFV termed pA/CP7_E1E2alf_TLA, which has a CSFV E2 protein comprising a mutated TAVSPTTLR epitope with the amino acid sequence: TLANKDTLA, as presented in SEQ ID NO: 3.

Therefore in an embodiment of the method according to the invention, the mutated TAVSPTTLR epitope of CSFV E2 that is comprised in the carrier for use in co-incubating, has the amino acid sequence: TAGSTLRTE (SEQ ID NO: 2).

In an alternate embodiment of the method according to the invention, the mutated TAVSPTTLR epitope of CSFV E2 that is comprised in the carrier for use in co-incubating, has the amino acid sequence: TLANKDTLA (SEQ ID NO: 3).

In a further embodiment, the test sample for the invention is derived from a porcine animal that had been vaccinated with a CSFV vaccine as described in Kortekaas et al. (2011, supra), such as a vaccine based on a mutant CSFV named: vFlc-ΔPTa1, as described above.

Therefore, in a further embodiment of the method according to the invention, the CSFV vaccine was based on the vFlc-ΔPTa1 virus.

The two different embodiments of a carrier described for use in the method according to the invention are: a carrier comprising a TAVSPTTLR epitope of CSFV E2, used for immobilising to a solid phase, and a carrier comprising a mutated TAVSPTTLR epitope of CSFV E2, used for co-incubating. These carriers can have different forms, and the carriers for the mutated- and for the wildtype TAVSPTTLR epitopes can be of the same or of different type; also they can be a separate, or can be the same entity, e.g. one carrier comprising both types of TAVSPTTLR epitopes.

In an embodiment of the method according to the invention, either the immobilised carrier comprising a TAVSPTTLR epitope of CSFV E2, or the carrier comprising a mutated TAVSPTTLR epitope of CSFV E2, is a protein, or both the carriers are proteins.

These proteins can be the same or different.

In a preferred embodiment of the method according to the invention, either the immobilised carrier comprising a TAVSPTTLR epitope of CSFV E2, or the carrier comprising a mutated TAVSPTTLR epitope of CSFV E2, is a CSFV E2 protein, or both the carriers are CSFV E2 proteins.

Apart from having a wildtype- or a mutated TAVSPTTLR epitope, the rest of a CSFV E2 protein carrier can also differ in amino acid sequences; several examples of CSFV E2 have been described in literature, and their sequences are available from public databases such as GenBank™.

When the immobilised carrier comprising a TAVSPTTLR epitope of CSFV E2 is a CSFV E2 protein, this provides the best opportunity for detecting antibodies against CSFV from the test sample.

Similarly, when the carrier comprising a mutated TAVSPTTLR epitope of CSFV E2, is a CSFV E2 protein, this provides the best opportunity for the capture of any cross-reactive antibodies that may be present in the animal test sample, and which would otherwise cause false positive results. This because a CSFV E2 protein will provide a 3D presentation of the mutated TAVSPTTLR epitope of CSFV E2 that is closest to the natural form of this epitope.

Therefore, in a preferred embodiment of the method according to the invention, both the carriers are complete mature CSFV E2 proteins.

However, as is known in the art, the C-terminal transmembrane region, and in fact the C-terminal half of E2, are less relevant for binding antibodies (van Rijn et al., 1994, J. of Virology, vol. 68, p. 3934; Chang et al., 2010, Virus Res., vol. 149, p. 183). Consequently, a skilled person will be well capable of developing and optimising a method for detecting wildtype CSFV antibodies according to the invention, in which either one, or none of the carriers is a complete mature E2 protein, but a part thereof—provided the (mutated) TAVSPTTLR epitope per se is still present, that still allows good detection of wildtype CSFV antibodies, and good reduction of false positive scores, in the context of the method according to the invention.

The use of a CSFV protein, or a part thereof, as a carrier comprising a (mutated) TAVSPTTLR epitope of CSFV E2 in the method according to the invention, can be further optimised by varying the amounts and conditions of the co-incubation. For example the inventor has expressed CSFV E2 protein with a mutated TAVSPTTLR epitope in the well-known baculovirus expression vector system, purified the protein, and used the recombinant expressed E2 protein for co-incubation assays.

Purity and quantity of the expressed E2 protein can be assessed, for example by SDS-gel-electrophoresis, protein staining, and quantitation by photo-densitometry. An alternative is quantification in an Elisa, using an antibody that binds to the E2, via another epitope than TAVSPTTLR, and reference samples of known concentration.

Depending on the purity of the protein, the amount of the E2 protein carrier comprising a (mutated) TAVSPTTLR epitope is chosen to obtain optimal detection of wildtype CSFV antibodies, while providing optimal reduction of false positive scores. As exemplified herein, typically less than 2 µg E2 protein was required per well of a 96 well microtitration plate. Amounts of 1 µg or even 0.5 µg per well were also effective.

As described, existing commercial diagnostic tests for wildtype CSFV antibodies have established their reliability based on a large body of test data for the determination of their sensitivity- and specificity profiles. This is maintained by internationally recognised sets of standard positive- and negative reference samples. The confidence in this combination of assay and reference samples is the basis for their marketing authorisation, and their use in government-controlled export certification of animals tested with such assays.

In order for the method according to the invention to achieve full integration with the reference values and prior test-scores of such established assays, a further adaptation to the test protocol can be made. In particular the incubation conditions in the assay protocol can be adapted to accommodate for the additional component in the co-incubation step wherein the mutated TAVSPTTLR epitope of CSFV E2 is introduced.

The inventor has found that without adapting the incubation conditions of said step, the method according to the invention is still functional, and highly effective in reducing false negative scores; however when testing established standard samples using the method according to the invention, then the precise OD scores obtained may deviate from previous results for those standards, either higher or lower. This is because the addition of an additional compound may require some volume of liquid to be added to the incubation mixture, this can cause a dilution of the incubation buffer and the components it may include, such as salts, stabiliser, detergent or blocking agents, resulting in a deviation from standard scores.

Therefore in an embodiment the method according to the invention comprises adapting the incubation conditions of the step comprising co-incubating with a carrier comprising a mutated TAVSPTTLR epitope of CSFV E2, to accommodate for the addition of said carrier.

There are several ways this "adapting" can be performed. The most direct one being to take up a solution comprising a carrier comprising a mutated TAVSPTTLR epitope of CSFV E2 into an incubation buffer for use in the method according to the invention, whereby the incubation buffer is at an increased concentration as compared to its final concentration when used in the method. For example, when combining equal volumes of a solution comprising a carrier comprising a mutated TAVSPTTLR epitope of CSFV E2, and of incubation buffer, then the incubation buffer can be provided as a stock solution at 2× the concentration of its final use. It may also be required to correct for any salts or buffers that are already present in the solution comprising the carrier comprising the mutated TAVSPTTLR epitope of CSFV E2. This principle is easily adapted to other volume ratios and corresponding concentrations for the incubation buffer stock solution.

Alternatively, a ready to use premixed solution may be provided of incubation buffer already comprising a carrier comprising a mutated TAVSPTTLR epitope of CSFV E2, wherein the incubation buffer is at its final use concentration.

The previous examples relied on providing the carrier comprising a mutated TAVSPTTLR epitope of CSFV E2 in a solution. However, as this may not be optimal for the stability of the protein, an alternative is to provide the protein comprising the mutated epitope of CSFV E2 in a separate container in freeze dried form, next to a container of incubation buffer at final use concentration. When the protein is then reconstituted with the incubation buffer shortly before use, this does not affect the protein's stability, and the reconstitution does not (noticeably) change the concentration of the incubation buffer.

A skilled person will be capable of devising and optimising other combinations to arrive at similar solutions.

As described, a favourable way of applying a method according to the invention is by using a diagnostic test kit, comprising the various components needed to apply the method.

Therefore a further aspect of the invention relates to a diagnostic test kit for implementing a method according to the invention.

For the invention, the "diagnostic test kit" relates to a kit of parts for performing the method according to the invention. The kit comprises one or more of the components for applying the method, in particular: a carrier comprising a TAVSPTTLR epitope of CSFV E2 that is immobilised to a solid phase, and a carrier comprising a mutated TAVSPTTLR epitope of CSFV E2. These should come in a convenient form and container, optionally with buffers for sample dilution and incubation, blocking, or washing, and optionally instructions how to perform the method, and how to read- and interpret the results.

In an embodiment the kit may comprise a container having multiple wells, such as a microtitration plate. The wells of the container may be treated to contain one or more components for use in the method according to the invention.

In a prefered embodiment of the diagnostic test kit according to the invention, a CSFV E2 protein with TAVSPTTLR epitope is immobilized to the wells of a microtitration plate.

The instructions optionally comprised with the diagnostic test kit according to the invention, may for example be written on a box containing the constituents of the kit; may be present on a leaflet in that box; or may be viewable on, or downloadable from, an internet website from the distributor of the kit, etc.

For the invention, the diagnostic test kit may also be an offer of the mentioned parts (relating to commercial sale), for example on an internet website, for combined use in an assay comprising the method according to the invention.

In an embodiment, a test kit according to the invention may be based on one of the known commercial test kits for wildtype CSFV E2 antibodies, i.e. be essentially the same as for example the PrioCHECK® CSFV Ab 2.0 (Prionics), or the IDEXX CSFV Ab Test® (IDEXX), with modification to accommodate for the co-incubation with additional component. The modification may relate to amended users' instructions, to provide instructions for co-incubating. Also, the kit may additionally provide a container comprising a freeze dried preparation comprising a carrier comprising a mutated TAVSPTTLR epitope of CSFV E2, to be resuspended e.g. in incubation buffer. Alternatively, the test kit may comprise a container with a stock solution of incubation buffer at a concentration that is higher than its final use concentration, and a container comprising a solution comprising a carrier comprising a mutated TAVSPTTLR epitope of CSFV E2, for use with the incubation buffer stock solution in the co-incubation. Several other embodiments to incorporate the components of the diagnostic test kit according to the invention are conceivable to a skilled person. Therefore, such embodiments fall within the scope of the present invention.

Therefore in an embodiment, the test kit according to the invention comprises a container comprising a carrier comprising a mutated TAVSPTTLR epitope of CSFV E2.

In a further aspect the invention relates to the use of a carrier comprising a mutated TAVSPTTLR epitope of CSFV E2 for co-incubating in a method according to the invention, or in a diagnostic test kit according to the invention.

Such a use provides for the detection of wildtype CSFV antibodies in animal test samples, especially for samples from animals that had been vaccinated against CSF with a CSFV vaccine comprising a CSFV E2 protein comprising a mutated TAVSPTTLR epitope. This use provides for a reduction of any false positive scores, as described.

In an embodiment, the use according to the invention relates to the use of a carrier comprising a mutated TAVSPTTLR epitope of CSFV E2. Preferably the carrier is a protein, and preferably the protein is a CSFV E2 protein, and preferably the CSFV E2 protein is a complete mature protein.

A further advantageous application of the method for detecting according to the invention is in its application to a DIVA approach for CSFV vaccination and detection. This allows for the differentiation between animals that are vaccinated against CSFV and that are infected with CSFV. It is only with the method according to the invention, and the subsequent elimination of false positive scores, that a serologic differentiation in this way is possible, when the vaccination was by use of a vaccine against CSF that comprises a CSFV E2 protein comprising a mutated TAVSPTTLR epitope.

Therefore, in a further aspect the invention relates to a method for differentiating between animals infected with wildtype CSFV and animals that were vaccinated against CSFV with a CSFV vaccine, whereby the vaccine comprises a CSFV E2 protein comprising a mutated TAVSPTTLR epitope, and the method is comprising the use of a method for detecting according to the invention, or is comprising the use of a diagnostic test kit according to the invention.

The method for differentiating according to the invention, is a method for in vitro diagnosis, using animal test samples as described above. The skilled person will realise that the method for differentiating according to the invention as such, involves results in diagnostic scores for the test samples investigated. In particular the detection of CSFV E2 protein antibodies, by either their presence or absence, or their level in absolute value, or a relative value in comparison to the value of a control sample.

Input for the method is a test sample from a subject; the subject preferably a porcine animal; the test sample preferably a blood sample, more preferably a sample of serum or plasma.

In order to make the final differentiation between infected and vaccinated animals, the test scores need to be interpreted as being positive or negative; in practice that means: being above or below a certain threshold. This can conveniently be done by incorporating into the test a number of standard reference samples to be tested alongside the test samples. This is described in the Examples. Positive and negative reference sample can be prepared in animals, or can be obtained from several institutions, and reference laboratories, for example the Community Reference Laboratory for CSF, at the University of veterinary medicine, Hannover, Germany.

After scoring the test samples as being positive, negative, or suspect, this can be extrapolated to diagnosing the donor animal from which the test sample was obtained, as being positive, negative, or suspect for infection with wildtype CSFV.

In case the animal is diagnosed as positive (or suspect), then-in line with governing regulations—the animal can be treated by vaccination and/or set aside in quarantine, or be culled in a responsible manner.

Therefore in an embodiment of the method for differentiating according to the invention, the method also comprises one or more steps selected from the following:
- a step for obtaining a test sample
- a step for the interpretation of obtained test results, by comparison to results of positive and of negative reference samples.
- a step for comparing obtained test results of the sample with a predetermined cut-off value,
- a step for scoring a sample as positive, negative, or suspect for containing antibodies against wildtype CSFV,
- a step for diagnosing a sample donor as being positive, negative or suspect for infection with wildtype CSFV, or
- a step for (recommending) treating a sample donor, based on a positive or suspect result from the diagnosis for infection with wildtype CSFV, by vaccination, quarantine, and/or culling.

In one or more preferred embodiments, the sample is a serum sample, or: the test results are scores of ELISA inhibition percentages In a preferred embodiment, the test sample is derived from a porcine animal that had been vaccinated against CSF with a CSFV vaccine comprising a CSFV E2 protein comprising a mutated TAVSPTTLR epitope.

In an alternate aspect the invention relates to an in vitro method for diagnosing infection with CSFV, the method comprising the use of a method for detecting according to the invention, or comprising the use of a diagnostic test kit according to the invention, and wherein the presence of antibodies against wildtype CSFV is determined in relation to the score of positive and negative reference samples.

In a further aspect of the invention, the method for detecting according to the invention, or the diagnostic test kit according to the invention, is employed for CSFV disease eradication, or in a national surveillance program, as a companion diagnostic, alongside the vaccination with a CSFV vaccine.

With this combination a DIVA approach for CSFV can be applied, which allows the differentiation between infected from vaccinated animals.

Therefore, in a further aspect, the invention relates to a method for controlling an infection with wildtype CSFV in a population of porcine animals, by the combined use of a CSFV vaccine comprising a CSFV E2 protein comprising a mutated TAVSPTTLR epitope, and a diagnostic test kit according to the invention.

As the invention provides for a strong reduction in false positive scores, (serum) samples from vaccinated animals can now be reliably identified as negative for antibodies against wildtype CSFV. Only truly positive animals need to be singled out, and subjected to appropriate control and quarantine measures in the context of surveillance-, stamping out-, or eradication programs.

Consequently this combined use of CSFV vaccine and diagnostic method allows the replacement of an undesirable and very costly stamping out policy by a structured vaccine-based CSFV eradication program, reducing animal suffering and economic costs.

The "population of porcine animals" can be taken as a group at local (farm), at regional, or even at national level. The details and the protocol for the "combined use" will depend on the vaccination protocol prescribed for the particular (marker) CSFV vaccine that is to be used. Also the performance of the combined use will be dependent on the requirements and the reason for the screening, or even on specific governmental regulations which may need to be complied with.

Some examples: in case of routine vaccination pigs will be vaccinated against CSFV once or twice at young age, and receive a booster vaccination e.g. at yearly intervals. These animals can be tested whenever suspicion of wildtype CSFV infection occurs. Alternatively: pigs meant for exportation that had been vaccinated, may be tested shortly before their intended exportation date. Also: in case of suspicion of CSFV infection or in CSFV outbreak situations, vaccination and testing may be performed within a short time interval, of weeks, maybe even days. These, and other embodiments conceivable to the skilled person, are all within the scope of the invention.

In practice, when a sample would score positive or negative for wildtype CSFV antibodies, confirmation may be obtained by retesting a sample from the same target, but from a different point in time, or by testing other animals from the same herd or area. Alternatively, the result can be confirmed using a different technique, and a different type of sample, e.g. by the detection of the virus in blood, tissue, nasal swaps, or faeces by virus neutralisation assay, or by the detection of viral nucleic acid. (e.g. by PCR)

The invention will now be further described by the following, non-limiting, examples.

EXAMPLES

Example 1: Testing of Porcine Samples 1.1. Test Samples:

The test samples used in Example 1 were obtained from the Central Veterinary Institute (Lelystad, the Netherlands), and are described in Kortekaas et al., 2011 (supra). In short: 8 week old seronegative pigs were vaccinated with live CSFV vaccines: either based on C-strain or on vFlc-ΔPTa1 virus. Blood-samples were taken throughout a number of weeks. Serum was prepared for testing. At 28 days after vaccination the animals were challenge infected with wildtype CSFV.

1.2. Prior Art ELISA Testing:

As described by Kortekaas et al., 2011 (supra), the porcine sera obtained were tested using a commercial ELISA: the PrioCHECK® CSFV Ab 2.0 (Prionics). This was performed according to the manufacturer's instructions, in short: precoated microtitration plates were used, and the kit's sample buffer was dispensed. Control samples were added to specific wells, and test samples (porcine serum) to other wells. Next the plates were incubated, washed, and conjugate was dispensed. Again plates were incubated and washed, and finally a colouring reagent was added, incubated and then stopped. Next plates were read by measuring OD. Percentages of ELISA inhibition were calculated based on the positive standard. Results are depicted in FIG. 1A, as comparative results, essentially reproducing FIG. 4A of Kortekaas et al., 2011 (supra). For this ELISA, the threshold for positive/negative separation is at 40% inhibition.

As is clear from these results: both the serum samples of C-strain vaccinated pigs (dotted lines), as well as the samples from pigs vaccinated with the vFlc-ΔPTa1 virus marker vaccine (solid lines), respond positive over time; i.e. induce 40% or more inhibition. Consequently no clear distinction could be made between animals that were vaccinated with C-strain vaccine or with marker CSFV vaccine (i.e. vFlc-ΔPTa1 virus).

1.3. Retesting of Prior Art Samples:

These serum samples of Kortekaas et al. 2011 (supra) were then retested using a different commercial ELISA for CSFV E2 antibodies: the IDEXX CSFV Ab Test® (IDEXX), according to the manufacturer's instructions, and with a protocol that is essentially the same as that of the Prionics ELISA described above.

Results are presented in FIG. 1B, and the grey horizontal bar indicates the threshold for positive/negative separation in this assay, whereby: negatives are at 30% inhibition or less; positives are at 40% or more inhibition; scores in-between 30 and 40% inhibition are suspect samples. Results where the level of inhibition is a negative value, represent samples with OD values higher than that of the negative control. These can be considered as zero % inhibition values.

As is clear from the graph, and similar to the results in the Prionics ELISA, almost all samples react positive over time; only one marker vaccinate (pig no. 3161) stayed completely negative. Two samples from pigs no. 3163 and 3164 gave a spike value at 42 or 49 days post vaccination, this may be related to a challenge reaction; samples could not be retested for lack of material.

1.4. E2 Proteins

E2 protein was produced for use in a co-incubation for the method according to the invention, from the E2 gene of CSFV virus from C-strain and from vFlc-ΔPTa1 virus. Initially, the nucleotide sequence of their E2 genes was codon optimized for expression in the Baculovirus-insect cell expression system, while using only silent mutations. Next DNA according to the optimized sequence was chemically synthesized and cloned into a pFastBac® plasmid (Life technologies), behind the polyhedrin promoter. The expression cassette was transferred by site-specific transposition into a recombinant bacmid DNA and amplified in DH10Bac Escherichia coli competent bacteria. Next, bacmid DNA was isolated, and used to transfect Sf9 insect cells. Recombinant Baculovirus obtained from the transfection supernatant was used to infect fresh Sf9 insect cells. Baculovirus was isolated and used to infect Sf21 insect cells cultured in 2 L bioreactors. Both E2 proteins were expressed in these bioreactor cultures, primarily in the supernatant. This was harvested, and the E2 protein was isolated by affinity column chromatography, over a Sepharose column that had been coupled with a TAVSPTTLR epitope specific monoclonal antibody. Purified E2 protein was harvested from the column, and quantified by an inhibition ELISA.

Using SDS-gel electrophoresis, the expressed and purified E2 protein was characterised: a single band of about 80 kDa was observed, at a purity of about 80%. The E2 was then quantified in an Elisa, next to weight standard samples. The recombinant expressed CSFV E2 protein with mutated TAVSPTTLR epitope could routinely be obtained as a purified stock solution of about 800 µg/ml.

1.5. Detection by Method According to the Invention:

The method for detecting antibodies against wildtype CSFV in a test sample according to the invention was applied on the samples of Kortekaas et al., 2011 (supra) described above.

The protocol was largely based on that for the IDEXX ELISA, with in addition the co-incubation. In short: the IDEXX CSF Ab Test Kit was employed according to the instructions of the manufacturer, with one exception: the kit's standard sample diluent was replaced by a 2× concentrated version. Then 25 µl (that is half the volume prescribed in the test kit's protocol) of this 2× sample diluent was co-incubated in the E2 coated wells with 50 µl serum sample and 25 µl of a solution of Baculovirus expressed CSFV E2 protein with mutated TAVSPTTLR epitope, such that about 1 µg E2/well was present.

The CSFV E2 protein with mutated TAVSPTTLR epitope that was used in these co-incubations was the E2 that is comprised in the vFlc-ΔPTa1 vaccine virus.

The results obtained are presented in FIG. 1C, and immediately illustrate the difference to the results of the same assay without co-incubation (FIG. 1B); or to a similar assay, without co-incubation (FIG. 1A). All samples from C-strain vaccinated pigs react positive, whereas all samples from marker vaccinated pigs react negative. No effect of the booster vaccination was found, and even the spike values observed for pigs no. 3163 and 3164 were below threshold.

In this way an effective DIVA test is finally possible for a live attenuated CSFV vaccine!

When this experiment was repeated using E2 protein from wildtype CSFV for co-incubating (not presented here), the results were altogether different: all samples scored negative, even the samples from C-strain vaccinated pigs. Consequently, this is not a useful alternative.

The introduction of the co-incubation was also made in the basic protocol of the PrioCHECK® CSFV Ab 2.0 ELISA (Prionics). Essentially the same results were observed: a very effective reduction of false positive results, leaving only true positive samples scoring positive (here: above 40% ELISA inhibition).

1.6. Summary of Results from Retesting of Prior Art Samples:

The results of the experiments as described above are assembled in Table 1. This reveals that the classification that the vaccinated animals from the Kortekaas 2011 (supra) experiment would receive, when tested for being positive/suspect for CSFV antibodies differs, depending on which method of detection of E2 antibodies would be applied. As is evident, only by using co-incubating with a carrier comprising a mutated TAVSPTTLR epitope of CSFV E2, can animals vaccinated with a CSFV vaccine comprising a CSFV E2 protein comprising a mutated TAVSPTTLR epitope, be clearly distinguished from animals there were wildtype CSFV infected- or C-strain vaccinated.

TABLE 1

Number of animals from Kortekaas 2011 experiment, scoring suspect or positive for CSFV antibodies using different methods for the detection of CSFV E2 antibodies.

| Method for detecting CSFV E2 antibodies | Wildtype vaccinated | Marker vaccinated |
|---|---|---|
| Prionics ELISA | 4/4 | 5/5 |
| IDEXX ELISA | 4/4 | 4/5 |
| IDEXX ELISA + co-incubation with wildtype E2 | 0/4 | 0/5 |
| IDEXX ELISA + co-incubation with mutated E2 | 4/4 | 0/5 |

Example 2: Establishing Test Specificity and -Sensitivity

To determine that the specificity and sensitivity of the methods according to the invention is at least comparable to that of a standard commercial CSFV E2 antibody ELISA, a large number of samples (about 900) were tested using one of the methods according to the invention. The samples were made available by Dr. W. L. Loeffen, from the collection of the Virology Division, Central Veterinary Institute, Lelystad, The Netherlands, and included a group of over 400 CSFV negative field pig sera from the Netherlands, a group of over 400 samples from experimentally CSFV infected pigs which were sampled over several weeks, and a group of about 80 pig serum samples of mixed origin; this last group contained positive and negative sera, from pigs vaccinated against- or infected with CSFV, as well as pigs infected with BVDV, or BDV strains, as well as some mixed infections.

For the application of the methods according to the invention, all samples were tested using the protocol and materials of the IDEXX CSF Ab Test Kit, using the pre-coated plates, positive and negative control samples, A18 monoclonal antibody conjugate, colour-reaction substrate, stop solution, and wash solution. Only deviation was that the sample diluent was replaced by a 2× concentrated version of that diluent, which was used at half of the volume as according to the test protocol; the other half of the volume was provided by the addition of a solution comprising CSFV E2 protein with a mutated TAVSPTTLR epitope, namely the E2 protein comprised in the vFlc-ΔPTa1 virus. Control samples were tested in duplo, test samples in single.

Interpretation of the ELISA inhibition results was the same as for the commercial ELISA: negatives are at 30% inhibition or less; positives are at 40% or more inhibition; scores in-between 30 and 40% inhibition are suspect samples.

Figure 2:
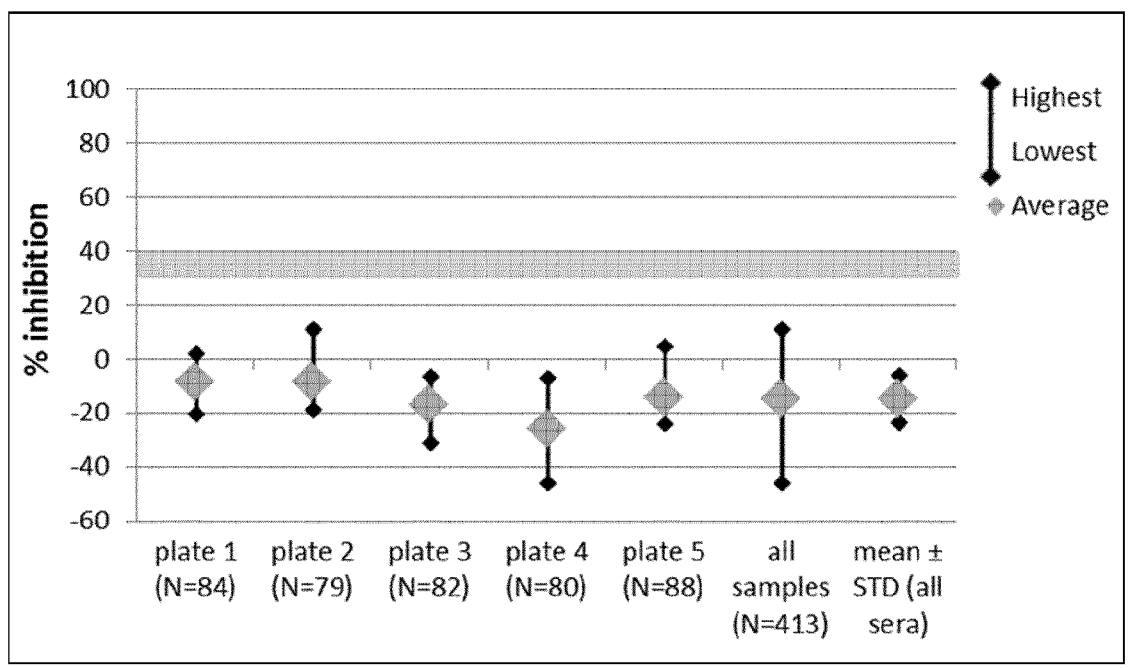

2.1. CSFV Negative Field Samples:

The group of negative field sera generally scored between −20 and 0% ELISA inhibition. Results are represented in FIG. 2. The mean score from the 413 samples was: −11%±5.2%. This was in line with expectations: all samples scored far below the threshold value for suspect/positives (30% ELISA inhibition), and the use of the method for detecting, and the method for differentiating, both according to the invention did not produce any false positive scores from true negative samples.

2.2. CSFV Positive Experimental Samples:

The analysis of a group of over 400 CSFV positive samples taken over time, proved the sensitivity of the methods according to the invention is excellent. Results are presented in FIG. 3, and display that especially at early times post infection, the methods according to the invention provide results that allow more samples to be classified as positive and less samples to be classified as suspect or negative than a commercial CSFV E2 antibody ELISA. This is most prominent at 14 days post infection, and still somewhat at 21 days post infection.

Consequently this proves that the sensitivity of the methods according to the invention, in correctly detecting true positives, is at least as good as that of a commercial CSFV E2 antibody ELISA, or put differently: the introduction of the co-incubation into one step of an existing CSFV E2 antibody ELISA did not harm the test's sensitivity, on the contrary.

2.3. Mixed Samples:

One group of about 80 samples of various types was tested using the methods according to the invention, to compare the results to those from a standard commercial ELISA. The various samples were from panels known as 'Erns workshop', "CSFV EU reference panel", and the CVI Lelystad internal 'Pestivirus reference panel'.

Samples and their codes are listed in Table 2, along with the results from the detection of antibodies against CSFV E2, using either the methods according to the invention (indicated in the column 'Invention'), or using a commercial CSFV E2 antibody ELISA (indicated in the column 'Commercial'). The column with sample numbers is for reference purpose only: samples 1-54 are sera from field samples of animals infected with different strains of CSFV, or vaccinated against CSFV; samples were taken at different days post infection (dpi) or days post vaccination (dpv); samples 55-60 are true negatives; samples no. 61-67 are sera from infections with BVDV; sample 68 from BDV infection; and samples 69-76 from mixed infections.

Results are presented as percentage ELISA inhibition score, and classified according to the scoring schedule of the commercial ELISA.

As is clear from the results in Table 2, for the vast majority of the samples tested, the results obtained using the methods according to the invention yielded scores for ELISA inhibition percentage with more distinction than the commercial ELISA. In only two cases the results using the method according to the invention deviated in a negative way, compared to the commercial ELISA: samples 23 and 75. It is not known if these were errors in test performance. Consequently, the methods according to the invention are at least as sensitive as a commercial ELISA for CSFV E2 antibodies.

This can have significant consequences, as for several samples the commercial ELISA and the methods according to the invention gave rise to different classifications. Examples are: sample no's: 8, 25, 28, 38, and 45, which were classified as 'suspect' by commercial ELISA, but according to the methods of the invention would need to be classified as 'positive' for CSFV E2 antibodies. Similarly, sample no. 37 would need a change in classification from negative to suspect.

For only two samples, no's. 23 and 75, the result of the method according to the invention was negative, while the score by commercial E2 antibody ELISA was positive. An experimental error, in either of the assays, may be a cause.

TABLE 2

Results of detection of CSFV E2 antibodies in set of mixed samples, expressed by ELISA inhibition percentage.

| # | Serum sample origin/type | Invention | Commercial |
|---|---|---|---|
| 1 | pr 83-01/Denissen 49 dpi/CSFV | 105 | 94 |
| 2 | pr 86-01/Alfort 120 dpi/CSFV | 105 | 94 |
| 3 | pr 96-16/cedipest 28 dpi/CSFV | 69 | 48 |
| 4 | pr 96-16/cedipest 28 dpi/CSFV | 81 | 51 |
| 5 | pr 96-16/cedipest 28 dpi/CSFV | 61 | 53 |
| 6 | pr. 96-04/v. Zoelen 46 dpi/CSFV | 96 | 77 |
| 7 | pr 95-05/E2-vacc. 35 dpi/CSFV | 95 | 84 |
| 8 | pr 95-05/E2-vacc. 35 dpi/CSFV | 48 | 31 |
| 9 | pr 95-05/E2-vacc. 35 dpi/CSFV | 76 | 56 |
| 10 | pr 96-05/Bergen 28 dpi/CSFV | 89 | 72 |
| 11 | pr 96-05/Bergen 28 dpi/CSFV | 77 | 56 |
| 12 | pr 96-05/Bergen 35 dpi/CSFV | 76 | 61 |
| 13 | pr 96-04 v. Zoelen 27 dpi/CSFV | 76 | 52 |
| 14 | pr 96-04 v. Zoelen 27 dpi/CSFV | 89 | 68 |
| 15 | pr 96-04 v. Zoelen 27 dpi/CSFV | 76 | 48 |
| 16 | pr 96-06/Henken 28 dpi/CSFV | 77 | 50 |
| 17 | pr 96-06/Henken 28 dpi/CSFV | 78 | 53 |
| 18 | pr 96-06/Henken 28 dpi/CSFV | 82 | 56 |
| 19 | pr 96-06/Henken 28 dpi/CSFV | 86 | 62 |
| 20 | pr 98-04/Cedipest 49 dpv/CSFV | 74 | 59 |
| 21 | pr 98-04/Cedipest 49 dpv/CSFV | 88 | 71 |
| 22 | pr 98-04/Cedipest 49 dpv/CSFV | 96 | 83 |
| 23 | pr 98-04/Cedipest 49 dpv/CSFV | 7 | 48 |
| 24 | pr 98-04/Cedipest 49 dpv/CSFV | 82 | 64 |
| 25 | pr 98-08/isolat 97-01 (Melis) 14 dpi/CSFV | 52 | 38 |
| 26 | pr 98-08/isolat 97-01 (Melis) 18 dpi/CSFV | 74 | 63 |
| 27 | pr 98-08/isolat 97-01 (Melis) 15 dpi/CSFV | 23 | 10 |
| 28 | pr 98-08/isolat 97-01 (Melis) 18 dpi/CSFV | 51 | 37 |
| 29 | pr 98-08/isolat 97-01 (Melis) 14 dpi/CSFV | 6 | 16 |
| 30 | pr 98-08/isolat 97-01 (Melis) 18 dpi/CSFV | 12 | 4 |
| 31 | pr 98-08/isolat 97-01 (Melis) 18 dpi/CSFV | 72 | 47 |
| 32 | pr 98-08/isolat 97-01 (Melis) 18 dpi/CSFV | 79 | 55 |
| 33 | CSF D33 | 79 | 67 |
| 34 | CSF D14 | 36 | 24 |
| 35 | CSF D21 | 41 | 27 |
| 36 | CSF D26 | 87 | 61 |
| 37 | CSF D15 | 39 | 25 |
| 38 | CSF D21 | 58 | 38 |
| 39 | CSF D29 | 95 | 76 |
| 40 | CSF D18 | 75 | 56 |
| 41 | CSF D20 | 77 | 61 |
| 42 | CSF0123, 14 dpi | 45 | 41 |
| 43 | CSF0277, 17 dpi | 86 | 69 |
| 44 | CSF0650, 20 dpi | 76 | 52 |
| 45 | CSF0902, 21 dpi | 49 | 34 |
| 46 | CSF0123, 20 dpi | 73 | 53 |
| 47 | CSF0277, 25 dpi | 79 | 62 |
| 48 | CSF0902, 26 dpi | 85 | 62 |
| 49 | CSF0573, 26 dpi | 74 | 56 |
| 50 | CSF0104, 29 dpi | 89 | 69 |
| 51 | CSF0695, 33 dpi | 81 | 71 |

TABLE 2-continued

Results of detection of CSFV E2 antibodies in set of mixed samples, expressed by ELISA inhibition percentage.

| # | Serum sample origin/type | Invention | Commercial |
|---|---|---|---|
| 52 | CSF0573, 33 dpi | 85 | 69 |
| 53 | CSF0123, 43 dpi | 95 | 84 |
| 54 | CSF0104, 77 dpi | 94 | 87 |
| 55 | pr 90-07/te Breteler/BVDV | 8 | -7 |
| 56 | pr. 83-04/Borgers/BVDV | 6 | 24 |
| 57 | pr. 83-04/Borgers/BVDV | 2 | -13 |
| 58 | pr. 83-04/den Otter/BVDV | 12 | 0 |
| 59 | pr 83-04/Kossink/BVDV | 1 | -5 |
| 60 | pr 83-04/Poels/BVDV | 20 | 29 |
| 61 | BVD D69 | 0 | 18 |
| 62 | BVD D34 | 15 | -6 |
| 63 | BVD D69 | 1 | 2 |
| 64 | BVD 10421/96, 34 dpi | -11 | 0 |
| 65 | BVD NADL/Osloss, 179 dpi | 3 | 2 |
| 66 | BVD Arnsberg, 69 dpi | -8 | -2 |
| 67 | BVD II Giessen, 64 dpi | -5 | -7 |
| 68 | BD "F | -9 | 1 |
| 69 | pr 94-13/strain "F"/BDV | 9 | -1 |
| 70 | pr 94-13/strain "F"/BDV | 58 | 45 |
| 71 | pr 94-13/strain "F"/BDV | 85 | 75 |
| 72 | pr 97-17/veld CSFV-BVDV | 3 | 15 |
| 73 | pr 97-17/veld CSFV-BVDV | 12 | 29 |
| 74 | pr 97-17/veld CSFV-BVDV/CSFV 28 dpi | 83 | 73 |
| 75 | pr 97-17/veld CSFV-BVDV/CSFV 28 dpi | 14 | 41 |
| 76 | BD + CSF D20 | 80 | 56 |

LEGEND TO THE FIGURES

FIG. 1:

Results of analyses by blocking ELISA for CSFV E2 antibodies in samples described by Kortekaas et al., 2011 (supra): compared are analyses by standard commercial assays, and analysis by the method according to the invention.

Dashed lines represent results from samples of pigs vaccinated with C-strain CSFV vaccine, the 'CS' samples; solid lines depict results from samples of pigs vaccinated with marker vaccine based on the vFlc-ΔPTa1 virus, the 'VS' samples.

The horizontal grey bars indicate the threshold scores in the different assays, for interpretation of samples as being positive, suspect, or negative for wildtype CSFV E2 antibodies.

FIG. 1A: Comparative results: reproduction of FIG. 4A from Kortekaas et al., 2011 (supra). The E2 ELISA used was the PrioCHECK® CSFV Ab 2.0 (Prionics).

FIG. 1B: Results of retesting of samples from Kortekaas et al., 2011 (supra), using a different commercial E2 ELISA, the IDEXX CSFV Ab Test® (IDEXX).

FIG. 1C: Results of retesting of samples from Kortekaas et al., 2011 (supra) using the method for detecting according to the invention: a co-incubation was introduced into one step of the IDEXX CSFV Ab Test.

FIG. 2:

Results from analysis of CSFV antibody in over 400 negative field samples. The test was performed according to the protocol for the IDEXX CSFV Ab Test® (IDEXX), with as modification the co-incubating in a method according to the invention. Results are indicated as the averages of the ELISA inhibition percentage detected per microtitration plate, with a result for all samples combined, and one for all plates combined. The highest and lowest values are indicated by black diamonds, connected by black bar, and averages by a grey diamond.

FIG. 3:

Results of analysis of over 400 samples from pigs experimentally infected with CSFV, and sampled at 2, 3, or 4 weeks post inoculation. Not from every animal there were three samples available. The method of detection was either the method according to the invention, indicated as 'Inv.'; or was a commercial ELISA (IDEXX CSFV Ab Test), indicated as 'Comm.'. The classifications: negative, suspect, and positive were based on the percentage ELISA inhibition measured, and assigned according to the scoring schedule of the commercial ELISA, respectively as less than 30%, 30-40%, or more than 40% ELISA inhibition.

The invention claimed is:

1. A method for detecting antibodies against wildtype classical swine fever virus (CSFV) in a test sample, whereby said sample may also comprise antibodies against a mutated TAVSPTTLR epitope of CSFV E2, the method comprising a step for incubating said test sample with an immobilized carrier comprising a TAVSPTTLR epitope of CSFV E2 comprising the amino acid sequence of SEQ ID NO: 1; wherein the method comprises co-incubating in said step with a carrier comprising a mutated TAVSPTTLR epitope of CSFV E2 comprising the amino acid sequence selected from the group consisting of SEQ ID NO: 2 and SEQ ID NO: 3.

2. The method of claim 1, wherein the detection is performed by ELISA (enzyme linked immunosorbant assay).

3. The method of claim 1, wherein the test sample is obtained from a porcine animal that had been vaccinated against CSF with a CSFV vaccine comprising a CSFV E2 protein comprising the mutated TAVSPTTLR epitope.

4. A diagnostic test kit for implementing the method of claim 3.

5. The method of claim 1, wherein the mutated TAVSPTTLR epitope of CSFV E2 that is comprised in the carrier for use in co-incubating, is the same as the mutated TAVSPTTLR epitope comprised in the CSFV E2 protein of a CSFV vaccine that was used to vaccinate the porcine animals from which the test sample was obtained.

6. The method of claim 5, wherein the CSFV vaccine was based on the vFlc-ΔPTa1 virus.

7. A diagnostic test kit for implementing the method of claim 5.

8. The method of claim 1, wherein the mutated TAVSPTTLR epitope of CSFV E2 that is comprised in the carrier for use in co-incubating comprising the amino acid sequence of TAGSTLRTE (SEQ ID NO: 2).

9. The method of claim 8, wherein the CSFV vaccine was based on a vFlc-ΔPTa1 virus.

10. A diagnostic test kit for implementing the method of claim 8.

11. The method of claim 1, wherein either the immobilised carrier comprising a TAVSPTTLR epitope of CSFV E2, or the carrier comprising a mutated TAVSPTTLR epitope of CSFV E2, is a CSFV E2 protein, or wherein both the carriers are CSFV E2 proteins.

12. The method of claim 1, comprising adapting the incubation conditions of the step comprising co-incubating with a carrier comprising the mutated TAVSPTTLR epitope of CSFV E2, to accommodate for the addition of said carrier.

13. A diagnostic test kit for implementing the method of claim 1.

14. A method for controlling an infection with wildtype CSFV in a population of porcine animals, by the combined use of a CSFV vaccine comprising a CSFV E2 protein comprising a mutated TAVSPTTLR epitope, and the diagnostic test kit of claim 13.

\* \* \* \* \*

SEQUENCE LISTING

```
<160> NUMBER OF SEQ ID NOS: 3

<210> SEQ ID NO 1
<211> LENGTH: 9
<212> TYPE: PRT
<213> ORGANISM: Classical swine fever virus

<400> SEQUENCE: 1

Thr Ala Val Ser Pro Thr Thr Leu Arg
1               5

<210> SEQ ID NO 2
<211> LENGTH: 9
<212> TYPE: PRT
<213> ORGANISM: Artificial Sequence
<220> FEATURE:
<223> OTHER INFORMATION: mutated TAVSPTTLR epitope from CSFV E2 protein

<400> SEQUENCE: 2

Thr Ala Gly Ser Thr Leu Arg Thr Glu
1               5

<210> SEQ ID NO 3
<211> LENGTH: 9
<212> TYPE: PRT
<213> ORGANISM: Artificial Sequence
<220> FEATURE:
<223> OTHER INFORMATION: mutated TAVSPTTLR epitope from CSFV E2 protein

<400> SEQUENCE: 3

Thr Leu Ala Asn Lys Asp Thr Leu Ala
1               5
```